United States Patent
Lindbo

(10) Patent No.: US 11,179,321 B2
(45) Date of Patent: *Nov. 23, 2021

(54) AVOIDING GAG REFLEX TO ENABLE SWALLOWING PILLS

(71) Applicant: Glen D Lindbo, Honolulu, HI (US)

(72) Inventor: Glen D Lindbo, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/101,536

(22) Filed: Nov. 23, 2020

(65) Prior Publication Data

US 2021/0069097 A1 Mar. 11, 2021

Related U.S. Application Data

(63) Continuation of application No. 16/354,124, filed on Mar. 14, 2019, now Pat. No. 10,857,092.

(51) Int. Cl.
*A61K 9/28* (2006.01)
*A61K 9/46* (2006.01)
*A61K 9/20* (2006.01)

(52) U.S. Cl.
CPC .......... *A61K 9/0007* (2013.01); *A61K 9/2013* (2013.01); *A61K 9/2018* (2013.01); *A61K 9/282* (2013.01); *A61K 9/2813* (2013.01); *A61K 9/2826* (2013.01)

(58) Field of Classification Search
CPC .... A61K 9/007; A61K 9/2826; A61K 9/2013; A61K 9/2018; A61K 9/282
See application file for complete search history.

(56) References Cited

U.S. PATENT DOCUMENTS 6,641,838 B2 * 11/2003 Pather .................. A61K 9/0007
424/458

* cited by examiner

*Primary Examiner* — Ali Soroush
(74) *Attorney, Agent, or Firm* — Martin E. Hsia; Keri Ann K. S. Krzykowski

(57) ABSTRACT

Compositions and methods to avoid the gag reflex to enable swallowing of pills, by applying an edible coating to the pill that generates bubbles, so that the bubbles prevent direct contact of the pill with the back of the mouth, thereby avoiding the gag reflex. Preferably the coating generates bubbles from an acid-base reaction, from compressed bubbles entrapped in hard candy, or from any other manner for creating fizzing, effervescent or popping confectionary or other food products. Optionally the coating can have a strong taste, such as by being sour, to distract away from the gag reflex. Optionally, a time release envelope is provided to delay bubbling or to block atmospheric humidity.

3 Claims, 2 Drawing Sheets

US 11,179,321 B2

AVOIDING GAG REFLEX TO ENABLE SWALLOWING PILLS

This application is a continuation of U.S. patent application Ser. No. 16/354,124 filed Mar. 14, 2019.

TECHNICAL FIELD

The present invention relates to compositions or matter and methods to avoid the gag reflex, so that persons with a sensitive gag reflex can swallow pills. As used herein, the term pills includes (without limitation) pills, capsules, lozenges, and all other objects intended to be swallowed whole, such as encapsulated cameras, transmitters or other instruments.

BACKGROUND ART

Most humans have a gag reflex, which is technically called the pharyngeal reflex or laryngeal spasm. This is an involuntary reflex contraction of the back of the throat, evoked in response to an object contacting the back of the mouth (the rear of the oral cavity). The back of the mouth includes (without limitation) the back of the tongue, the soft palate, the area around the tonsils, the uvula, and the back of the throat. The gag reflex usually is not under voluntary control and prevents objects in the mouth from entering the throat, except as part of normal swallowing.

A substantial portion of the population has a sensitive gag reflex and therefore cannot swallow pills—placing the pills in the mouth and/or attempting to swallow pills whole triggers the gag reflex, because the pills contact the back of the mouth. This can create very serious problems because many medications must be taken in the form of pills, and many of the medications in these pills cannot be chewed, ground into powders, or changed to other physical forms such as liquids, because, for example, they have a coating for timed release of the medication in the stomach. This sensitive gag reflex also creates problems with dental procedures.

Many attempts have been made to overcome or avoid the problems created by a sensitive gag reflex.

One approach has been to swallow appropriately buoyant pills with water while the head is bowed downwardly, as disclosed in U.S. Pat. No. 3,418,999 to Davis, incorporated herein by reference. As stated therein in column 2, lines 28-31, "Since the pill is buoyed up and supported by the water, there is very little mouth or throat contact, hence it produces little or no sensation from its presence." However, this method is restricted to pills that are buoyant, that is, that float on water, but not so buoyant as to press against the tissues of the mouth or throat, as described in column 3, lines 39-42.

Another approach has been to make pills slippery. U.S. Pat. No. 9,393,209 B1 to Gath, incorporated herein by reference, discloses a pill-enveloping material that becomes slippery when in contact with water or saliva to aid in swallowing pills.

Another approach has been to provide a sensory stimulus elsewhere on the body to distract away from the back of the mouth. For example, U.S. Pat. No. 6,382,215 B1 to Morrish, incorporated herein by reference, discloses a method of suppression and prevention of the gag reflex using a non-invasive nerve stimulation device applied to the wrist.

Still another approach has been to provide specialized apparatus to assist in swallowing. For example, U.S. Pat. No. 7,431,175 to Heilos, incorporated herein by reference, discloses a drinking cup lid for assisting in the ingestion of medication.

However, none of the above approaches is usable with a large variety of sizes and buoyancies of pills, or with non-buoyant pills.

Thus, there is a long-felt but unmet need for a coating or other composition for a pill that would allow those with a sensitive gag reflex to easily swallow a pill, without the need for specialized apparatus.

It is well known that, in water (aqueous solution), acids react with bases to form carbon dioxide, which forms bubbles. This is called the acid-base reaction, or a neutralization reaction. This reaction has been used for many years to create effervescent or fizzing confectionaries or foods, such as sherbet powder (similar to candy marketed as Pixy Stix), or fizzy hard candy (Zotz or Soda Can). The acid-base reaction is also used in some pharmaceuticals or medicines, such as Alka Seltzer.

Food additives listed in the International Numbering System for Food Additives published in the Codex Alimentarius (which is recognized by the World Trade Organization) that are either acids or bases can be combined to create bubbles through the acid-base reaction.

Acids that are approved by governmental authorities for use as additives in food or pharmaceuticals are referred to herein as "food acids", and include citric acid, acetic acid (vinegar), phosphoric acid, folic acid, fumaric acid, malic acid, tartaric acid and lactic acid.

Bases that are approved by governmental authorities for use as additives in food or pharmaceuticals are referred to herein as "food bases", and include sodium bicarbonate (baking soda), magnesium hydroxide, magnesium carbonate, aluminum hydroxide, sodium carbonate, and other antacids.

A food acid and a food base can be incorporated in a soluble edible solid, so that saliva dissolves the solid and causes the food acid and the food base to generate bubbles of carbon dioxide.

Another type of edible product that forms bubbles is popping candy, which is made from hard candy containing bubbles of compressed gas, usually carbon dioxide, such as Pop Rocks.

U.S. Pat. No. 3,012,893 to Kremzner, et al., incorporated herein by reference, discloses a gasified confection, in which gas at superatmospheric pressure is captured in solidified fused sugar, which has been sold under the trademark "Pop Rocks".

U.S. Pat. No. 4,289,794 to Kleiner, et al., incorporated herein by reference, discloses a gasified candy with a more pronounced popping sensation with larger gas bubbles.

International patent application PCT/US2001/014887 to Gilleland, et al., incorporated herein by reference, discloses film forming compositions comprising starch derivatives and an external plasticizer.

All generating of bubbles, including fizzing, foaming, and popping, regardless of the mechanism of generating the bubbles (including those described above, their equivalents, and others) is sometimes singly and collectively referred to as bubble generating or effervescing.

All products that can be swallowed as part of a coating of a pill, without substantial harm, are hereinafter referred to as edible.

BRIEF DISCLOSURE OF THE INVENTION

In a first presently preferred embodiment, the present invention is a composition of matter to avoid the gag reflex, comprising a pill and a bubble generating edible coating covering the pill, wherein the bubbles prevent the pill from directly contacting the back of the mouth and thereby avoid triggering the gag reflex. Preferably, the coating generates bubbles in the presence of a liquid, including but not limited to saliva or water, such as a liquid that a user drinks together with the pill, or a liquid to which the pill is exposed before being placed in the mouth. Preferably also, the bubble generating edible coating is selected from the group consisting of a soluble edible solid containing pressurised gas bubbles, and a soluble edible solid containing a food acid and a food base. Preferably, the soluble edible solid comprises solidified fused sugar. Preferably, the food acid is selected from the group consisting of citric acid, acetic acid, phosphoric acid, malic acid, fumaric acid, lactic acid, and tartaric acid. Optionally, the edible coating is sour.

Optionally also, a time release envelope can be provided that delays generating of bubbles for a time, preferably approximately 15 seconds, after the pill with the bubble generating edible coating and time release envelope have been exposed to a liquid, such as saliva, which dissolves the time release envelope.

This time release envelope preferably blocks atmospheric humidity from contacting the bubble generating edible coating. Also, this time release envelope allows a person to place the pill (with bubble generating edible coating and time release envelope) in the front of the mouth (such as on the front of the tongue) and take a sip of water or other liquid, and then wait for the time release envelope to dissolve (so that the bubble generating edible coating starts bubbling) before swallowing the water or other liquid, with the pill. The time release envelope can be made from any suitable soluble edible material, such as sugar, gelatin, or candy, such as chocolate.

In a second presently preferred embodiment, the present invention is a composition of matter to avoid the gag reflex, comprising a medicine and a bubble generating soluble edible solid mixed with the medicine and compressed and bound together to form a pill, wherein the solid generates bubbles, wherein the bubbles prevent the pill from directly contacting the back of the mouth and thereby avoid triggering the gag reflex. Preferably, the bubble generating soluble edible solid generates bubbles in the presence of saliva. Preferably, the bubble generating edible solid is selected from the group consisting of a soluble edible solid containing pressurized gas bubbles, and a soluble edible solid containing a food acid and a food base. Preferably, the soluble edible solid comprises solidified fused sugar. Preferably, the food acid is selected from the group consisting of citric acid, acetic acid, phosphoric acid, malic acid, fumaric acid, lactic acid, and tartaric acid. Preferably, the soluble edible solid is sour.

In another aspect, the present invention is a coating for a pill to enable swallowing the pill without triggering the gag reflex, comprising an edible bubble generating coating that covers the surface of the pill. Preferably, the coating covers the entire surface of said pill.

In still another aspect, the present invention is a process for enabling swallowing a pill without triggering the gag reflex, comprising covering the pill with a bubble generating edible coating that generates bubbles when in contact with saliva, wherein the bubbles prevent the pill from directly contacting the back of the mouth, whereby triggering the gag reflex is avoided. The process can further comprise enveloping the bubble generating edible coating with a time release envelope that dissolves a delay time after being exposed to a liquid. Preferably, the covering step is performed using a bubble generating edible coating selected from the group consisting of a soluble edible solid containing pressurized gas bubbles, and a soluble edible solid containing a food acid and a food base.

BEST MODE FOR CARRYING OUT THE INVENTION

Figure 1:
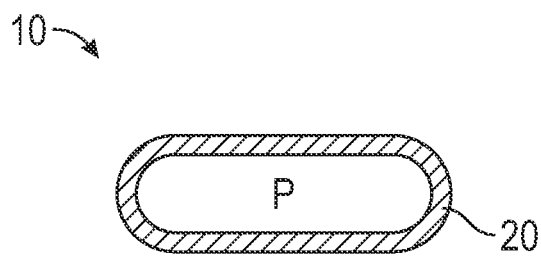
FIG. 1 is a cutaway view of a pill with a presently preferred embodiment of a coating according to the present invention.

The presently preferred best mode for practicing the present invention is illustrated by way of example in FIG. 1, which is a cutaway view of a pill P provided with a coating 20 according to the presently preferred embodiment of the present invention. Preferably, coating 20 comprises a bubble generating edible coating, such as an edible food acid and an edible food base. Preferably, the coating 20 generates bubbles in the presence of saliva. Alternatively, the coating 20 can generate bubbles in the presence of some other substance, such as a liquid to which the pill P and coating 20 are exposed before swallowing, to initiate effervescence, so that the pill is effervescing before being placed in the mouth. Optionally, the coating 20 can be made of a material with a strong taste, such as being sour, to distract away from the gag reflex.

Figure 2:
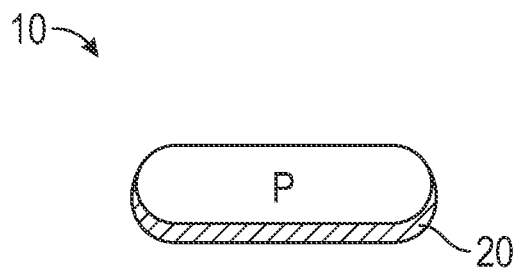
FIG. 2 is a cutaway view of a pill with an alternative embodiment of a coating according to the present invention.

Referring to FIG. 2, shown is a cutaway view of an alternative embodiment of the present invention 10 in which the coating 20 partially covers the pill P.

Figure 3:
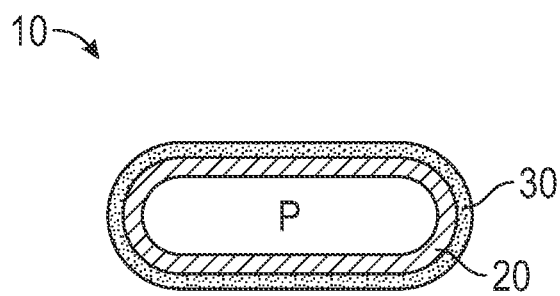
FIG. 3 is a cutaway view of a pill with a presently preferred embodiment of a coating according to the present invention, with a time release envelope.

Referring to FIG. 3, shown is a cutaway view of a presently preferred embodiment of the present invention 10, comprising a pill P with a bubble generating edible coating 20, and a time release envelope 30 enveloping the coating 20.

Figure 4:
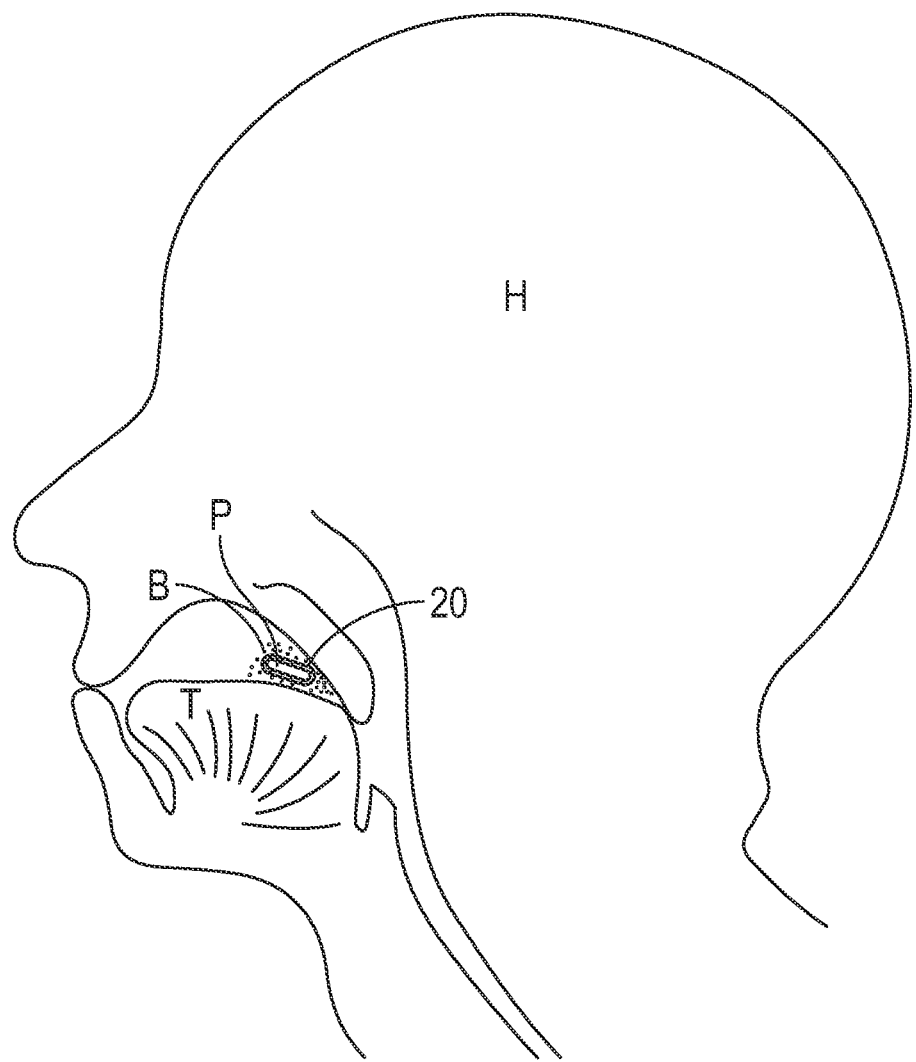
FIG. 4 is a diagrammatic view of a person's head with a pill having a coating according to the present invention placed in the back of the mouth, with bubbles preventing direct contact with the back of the mouth.

Referring to FIG. 4, shown is a diagrammatic view of a person's head H showing the coating 20 effervescing (either because there was no time release envelope, or the envelope has dissolved) and creating bubbles B that prevent direct contact between the pill P and the back of the mouth, such as the back of the tongue T. This allows the pill P and its coating 20 to be swallowed, without provoking the gag reflex.

It is believed that the present invention works by avoiding direct contact of the pill with the back of the mouth, or by the fizzing, foaming, popping or other effervescence distracting away from the gag reflex, or it may work by some other mechanism, such as a strong taste (such as being sour) that distracts away from the gag reflex, or the placebo effect. It may also work for different people for different reasons, and may not work for some people at all. However, the validity and enforceability of this patent shall not be affected if the mechanism by which this invention works is some other mechanism, or because this invention does not work for some people at all.

INDUSTRIAL APPLICABILITY

The present invention is applicable whenever it is desired to provide compositions or methods to avoid triggering the gag reflex, to enable swallowing of pills.

What is claimed is:

1. A process for enabling swallowing a pill having a volume in the range of about 0.2 cubic centimeters to about 1.7 cubic centimeters to be swallowed whole without triggering the gag reflex, consisting of:
   covering the pill having a volume in the range of about 0.2 cubic centimeters to about 1.7 cubic centimeters with a bubble generating edible coating that dissolves and generates bubbles when in contact with liquid, wherein said bubbles prevent the pill that is to be swallowed whole from directly contacting the back of the mouth, whereby triggering the gag reflex is avoided.

2. The process according claim 1, further comprising:
   enveloping said bubble generating edible coating with a time release envelope that dissolves a delay time after being exposed to the liquid.

3. The process according to claim 1, wherein said covering step is performed using a bubble generating edible coating selected from the group consisting of a soluble edible solid containing pressurized gas bubbles, and a soluble edible solid containing a food acid and a food base.

* * * * *